United States Patent
Volkl et al.

(10) Patent No.: US 10,485,640 B2
(45) Date of Patent: Nov. 26, 2019

(54) METHOD FOR PRODUCING A BLANK, BLANK AND A DENTAL RESTORATION

(71) Applicant: DENTSPLY SIRONA Inc., York, PA (US)

(72) Inventors: Lothar Volkl, Goldbach (DE); Martin Kutzner, Neuberg (DE); Tanja Oefner, Linsengericht (DE); Stefan Fecher, Johannesberg (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/388,282

(22) Filed: Dec. 22, 2016

(65) Prior Publication Data

US 2017/0258563 A1   Sep. 14, 2017

(30) Foreign Application Priority Data

Dec. 28, 2015 (DE) .................. 10 2015 122 861

(51) Int. Cl.
*A61C 13/08* (2006.01)
*A61C 13/00* (2006.01)
(Continued)

(52) U.S. Cl.
CPC ............ *A61C 13/0022* (2013.01); *A61C 5/73* (2017.02); *A61C 5/77* (2017.02); *A61C 8/0013* (2013.01); *A61C 13/081* (2013.01); *A61C 13/082* (2013.01); *A61C 13/083* (2013.01); *A61C 13/09* (2013.01); *B28B 3/021* (2013.01);
(Continued)

(58) Field of Classification Search
CPC ......... A61C 13/0022; A61C 5/77; A61C 5/73; A61C 8/0013; A61C 3/081; A61C 13/082; A61C 13/083; A61C 13/09; B32B 18/00; B28B 3/021; C04B 35/48; C04B 35/486; C04B 37/001
See application file for complete search history.

(56) References Cited

U.S. PATENT DOCUMENTS 4,921,655 A * 5/1990 Sterzel ................ C01B 21/0821
                                                    264/332
6,379,593 B1   4/2002 Datzmann
(Continued)

FOREIGN PATENT DOCUMENTS

| EP | 2371344 A1 | 10/2011 |
|---|---|---|
| WO | 2014062375 A1 | 4/2014 |
| WO | 2014137037 A1 | 9/2014 |

OTHER PUBLICATIONS

International Search Report; PCT/EP2016/082531; Mar. 9, 2017 (completed); dated Mar. 20, 2017.
(Continued)

*Primary Examiner* — Nicholas D Lucchesi
(74) *Attorney, Agent, or Firm* — Dentsply Sirona Inc.

(57) ABSTRACT

The invention relates to a method for the preparation of a blank of a ceramic material, wherein a first ceramic material and then a second ceramic material of different compositions are filled into a die and wherein the materials are pressed and after pressing are sintered. A layer of the first ceramic material is thereby filled into the die and a first cavity formed in the layer, the second ceramic material is then filled into the first open cavity and the materials pressed together and then heat-treated.

11 Claims, 6 Drawing Sheets

(51) Int. Cl.
  *A61C 13/083* (2006.01)
  *A61C 13/09* (2006.01)
  *A61C 5/77* (2017.01)
  *A61C 5/73* (2017.01)
  *B32B 18/00* (2006.01)
  *C04B 35/486* (2006.01)
  *A61C 8/00* (2006.01)
  *B28B 3/02* (2006.01)
  *C04B 35/48* (2006.01)
  *C04B 37/00* (2006.01)

(52) U.S. Cl.
  CPC .............. *B32B 18/00* (2013.01); *C04B 35/48* (2013.01); *C04B 35/486* (2013.01); *C04B 37/001* (2013.01); *C04B 2235/3217* (2013.01); *C04B 2235/3224* (2013.01); *C04B 2235/3225* (2013.01); *C04B 2235/3232* (2013.01); *C04B 2235/3239* (2013.01); *C04B 2235/3241* (2013.01); *C04B 2235/3244* (2013.01); *C04B 2235/3262* (2013.01); *C04B 2235/3272* (2013.01); *C04B 2235/3277* (2013.01); *C04B 2235/3279* (2013.01); *C04B 2235/3281* (2013.01); *C04B 2235/72* (2013.01); *C04B 2235/765* (2013.01); *C04B 2235/9607* (2013.01); *C04B 2235/9653* (2013.01); *C04B 2235/9661* (2013.01); *C04B 2237/348* (2013.01); *C04B 2237/58* (2013.01); *C04B 2237/84* (2013.01)

(56) References Cited

U.S. PATENT DOCUMENTS

| | | | |
|---|---|---|---|
| 8,025,992 B2 | 9/2011 | Engels | |
| 8,632,889 B2 | 1/2014 | Thiel | |
| 8,691,122 B2 | 4/2014 | Rheinberger | |
| 8,936,848 B2 | 1/2015 | Jung | |
| 2004/0106087 A1* | 6/2004 | Weigl | A61C 13/0004 433/218 |
| 2006/0008774 A1 | 1/2006 | Orth | |
| 2007/0234929 A1* | 10/2007 | Reinsch | C04B 41/009 106/1.18 |
| 2007/0292597 A1* | 12/2007 | Ritzberger | A61C 13/0022 427/2.29 |
| 2008/0303181 A1* | 12/2008 | Holand | A61C 13/0022 264/16 |
| 2009/0252644 A1* | 10/2009 | Petroll | A61K 6/0205 420/588 |
| 2010/0035210 A1* | 2/2010 | Suchan | A61C 9/00 433/201.1 |
| 2010/0084774 A1* | 4/2010 | Liu | B28B 3/021 264/1.25 |
| 2012/0175801 A1 | 7/2012 | Jahns | |
| 2012/0196244 A1 | 8/2012 | Khan | |
| 2013/0172441 A1* | 7/2013 | Takahata | A61C 13/0022 523/115 |
| 2014/0162216 A1* | 6/2014 | Craig | A61C 13/0022 433/201.1 |
| 2014/0328746 A1 | 11/2014 | Yamada | |
| 2014/0356815 A1 | 12/2014 | Spalt | |
| 2015/0182315 A1* | 7/2015 | Okada | A61C 13/087 433/202.1 |
| 2016/0228222 A1 | 8/2016 | Rolf | |
| 2017/0183270 A1* | 6/2017 | Wondraczek | A61C 5/77 |

OTHER PUBLICATIONS

International Preliminary Report on Patentability; PCT/EP2016/082531; Apr. 3, 2018 (completed).
Written Opinion of the International Searching Authority; PCT/EP2016082531; Mar. 9, 2017 (completed); dated Mar. 20, 2017.

\* cited by examiner

METHOD FOR PRODUCING A BLANK, BLANK AND A DENTAL RESTORATION

THE CROSS-REFERENCE TO RELATED APPLICATIONS

This patent application claims the benefit of and priority to German Patent Application No. 10 2015 122 861.0, filed on Dec. 28, 2015, which is herein incorporated by reference for all purposes.

TECHNICAL FIELD

The invention relates, inter alia, to a method for the preparation of a blank of a ceramic material, in particular a blank to be used for the preparation of a dental restoration, wherein a first ceramic material and then a second ceramic material of different compositions are filled into a die and wherein the materials are pressed and after pressing are sintered.

The invention also relates to a pre-sintered or fully-sintered blank to be used for the preparation of a dental restoration, such as a dental framework, crown, partial crown, bridge, cap, veneer, abutment, pin construction, in particular a crown or partial crown, comprising a ceramic material which in particular contains zirconium dioxide and has regions of different compositions.

BACKGROUND

U.S. Pat. No. 8,936,848 B2 discloses a blank of zirconium dioxide that is used for the preparation of a tooth replacement and comprises a number of layers of different chemical compositions. The individual layers thereby have different percentages of yttrium oxide.

A body of zirconium dioxide exhibits a decrease or increase in chromacity along a straight line in the L*a*b* color space (US 2014/0328746 A1).

A blank of zirconium dioxide for the preparation of dental objects in accordance with WO 2014/062375 A1 has at least two material regions which have different percentages of tetragonal and cubic crystal phases, wherein in one of the regions the quotient is greater than 1 and in the other region the quotient is lower than 1.

EP 2 371 344 A1 relates to a ceramic body which is enriched with a stabilizing agent from the surface to a desired depth.

Zirconium dioxide is used as a ceramic material to produce dental restorations. A framework can be milled, for example, from a blank of zirconium dioxide and can then be sintered. In the following processing stages, a veneer is applied manually to the framework, wherein at least one incisor material is applied and fused. All of these process measures are time-consuming and moreover do not ensure that the dental restoration will meet the requirements.

SUMMARY OF THE INVENTION

It is an object of the present invention to develop a method of the aforementioned type in such a way that the disadvantages of the prior art are avoided and in particular that a dental restoration can be produced from a ceramic material without laborious finishing, which satisfies aesthetic requirements and moreover is of high strength in regions under severe loads.

To achieve this aim it is proposed, inter alia, that a layer of a first ceramic material is filled into the die and that a first open cavity is formed in the layer, that the second ceramic material is filled into the first open cavity and that the materials are pressed together and are then heat-treated.

According to the invention, a layer of pourable material is first filled into a die. This may, for example, be a colorless zirconium dioxide granular material that has a bulk density between 1 $g/cm^3$ and 1.4 $g/cm^3$, in particular in the region between 1.15 $g/cm^3$ and 1.35 $g/cm^3$. Following filling of the granular material, which has a grain size D50 between 40 µm and 70 µm, an open cavity is formed, for example by means of a press plunger. This is carried out, for example, by expelling parts of the first ceramic material and/or lightly compacting them. Thus, in the so-formed recess or cavity, which in particular has a substantially conus-like geometry, the second ceramic material is filled, if a crown or partial crown is to be produced from the blank, the conus-like shaped recess or cavity is aligned with the geometry of a tooth stump or an abutment, so that the materials are pressed together.

There is also the possibility of forming a further, second open cavity in the second ceramic material that fills the first open cavity. This step can accompany the concomitant pressing of all materials.

Compaction of the materials takes place independently thereof.

Compression is preferably carried out at a pressure preferably between 1000 bar and 2000 bar. A density of approximately 3 $g/cm^3$ is attained. Debinding and pre-sintering at a temperature between 700° C. and 1100° C. are then carried out, in particular in a range between 800° C. and 1000° C., over a time between 100 minutes and 150 minutes.

The debinding and pre-sintering should be carried out in such a way that a breaking strength between 10 MPa and 60 MPa, in particular between 10 MPa and 40 MPa is achieved, measured in accordance with DIN-ISO 6872.

Where a second open cavity is formed in the second ceramic material and a third ceramic material is filled into it, then this composition should differ from that of the second ceramic material, in particular in having a lower translucence and/or a higher bending strength than the second/first material.

In particular, according to the invention a number of first open cavities are provided in the layer of the first ceramic material, and the second ceramic material is filled into these. This yields a number of distinct, separated blank sections, so-called nests, so that after the pre-sintering a number of dental restorations can be derived from the sections of such a blank, in particular through milling and/or grinding. Thereby it is possible for the dimensions of the blank sections to differ from one another to derive restorations of different geometries which can also differ in the geometric arrangement of the respective root-side/dentine-side material regions. It is therefore possible to obtain teeth of different shapes from one blank, according to the number of nests/blank sections and their geometries. As already mentioned, the dentine cores are formed from the second regions and the incisors from the first region.

The invention in particular provides for the thermal expansion coefficient of the second ceramic material to be 0.2 µm/m*K to 0.8 µm/m*K higher than the thermal expansion coefficient of the first ceramic material. As a result of the different thermal expansion coefficients of the materials, a compressive stress is created in the first material i.e. in the incisor material which leads to an increase in strength of the dental restoration derived from the blank.

Furthermore, there is the possibility of coloring the ceramic materials to the desired extent, in particular such that for the first region an incisor material is used which is more translucent and less colored compared to the second ceramic material.

If a dental restoration or other molded body is preferably derived from the pre-sintered blank, then there is naturally also the possibility that the blank is first fully-sintered to then produce the molded body, in particular by milling or grinding.

Independently of when the blank is sintered through, it is provided in particular for the complete sintering to be carried out over a period of between 10 minutes and 250 minutes at a temperature in the range between 1300° C. and 1600° C. Sintering may also be carried out at a slightly higher temperature.

If sintering is performed at a temperature which, for example, is 100° C. above the temperature given by the manufacturer of the starting material, and above the time recommended by the manufacturer for the complete sintering, this is referred to as over-sintering.

The present values apply in particular when the starting material substantially contains zirconium dioxide, in particular more than 80 wt %.

Yttrium oxide is in particular added to the zirconium dioxide, but calcium oxide, magnesium oxide and/or ceroxide may also be added.

If the ceramic material is colored, then in particular a color-imparting oxide from elements of the group Pr, Er, Tb, Fe, Co, Ni, Ti, V, Cr, Cu, Mn, preferably $Fe_2O_3$, $Er_2O_3$ or $Co_3O_4$ is used.

The invention is therefore also characterized by the fact that the ceramic materials used contain zirconium dioxide to which is added yttrium oxide ($Y_2O_3$), calcium oxide (CaO), magnesium oxide (MgO) and/or cerium oxide ($CeO_2$), in particular yttrium oxide, wherein the first ceramic material differs from the material of the second ceramic material in terms of color and/or crystal forms stabilized at room temperature.

Further, it is provided for the first and/or second ceramic material to be such that the percentage of yttrium oxide in the second material is in the range 4.5 wt % to 7.0 wt % and/or the percentage in the first material is in the range 7.0 wt % to 9.5 wt %, wherein the percentage of yttrium oxide in the first ceramic material is higher than that in the second material.

The materials of the first and also the second region should thereby be selected such that the quotient of the tetragonal crystal phase to the cubic crystal phase of zirconium dioxide of both regions after pre-sintering is ≥1.

The following composition in wt % is preferred as the basic material for the first and second ceramic material:

| | | |
|---|---|---|
| $HfO_2$ | | <3.0 |
| $Al_2O_3$ | | <0.3 |
| Technically caused, unavoidable components ≤0.2 (e.g., $SiO_2$, $Fe_2O_3$, $Na_2O$) | | |
| For the first layer: | $Y_2O_3$ | 7.0 to 9.5 |
| For the second layer: | $Y_2O_3$ | 4.5 to 7.0 |
| Coloring oxide: | | 0-1.5 |
| $ZrO_2$ = 100 − ($Y_2O_3$ + $Al_2O_3$ + $HfO_2$ + unavoidable components + color-imparting oxides) | | |

It is also possible for additional binding agents to be added. This is not taken into account in the above statement of percentage by weight.

According to the teaching of the invention, after full sintering a monolithic dental restoration is obtained, which in principle does not have to be veneered, but if so then there is no departure from the invention.

A pre-sintered or fully sintered blank for use in producing a dental restoration such as a dental framework, crown, partial crown, bridge, cap, veneer, abutment, pin construction, in particular crown or partial crown, consisting of a ceramic material, which in particular contains zirconium dioxide and regions of different compositions, wherein a first region is of a first ceramic material and at least one second region is of a second ceramic material and the regions are adjacent to each other, is characterized by the fact that at least one second region extends within the first region and has an outer geometry that tapers from a basal region. Thereby, the basal region should extend in the region of an outer surface of the first region, and preferably merge with it.

It is also possible for the second region extending from the basal region to have a cavity.

Independently of this, the second region in its outer geometry has a conus-like extending geometry.

There is also the possibility that a third region extends within the second region, said third region consisting of a third ceramic material of a composition which deviates from that of the second ceramic material.

It is to be emphasized and in accordance with this invention that a number of second regions are surrounded by the first region, in particular some of the plurality of second regions differ in their external geometries.

Thus, for example, crowns or artificial teeth of different geometries can be produced, which have a higher strength in the dentine than in the incisal region. For this purpose upon derivation of the dental restoration from the blank, the dentine is formed in the region of sections of the second region and the incisal region is formed from sections of the first region of the blank.

The invention is further characterized in that the blank contains zirconium dioxide to which yttrium oxide has been added, that the percentage of yttrium oxide in the second or third ceramic material lies between 4.5 wt % and 7.0 wt % and in the first ceramic material lies between 7.0 wt % and 9.5 wt %, wherein the percentage of yttrium oxide in the first ceramic material is greater than in the second ceramic material.

The lower yttrium content in the material of the second region results in a higher strength in comparison to that of the first region.

Furthermore, there is the possibility that the ceramic material of the second region is colored and that of the first region is colored to a lesser degree or not at all, so that a higher translucency than in the second region results.

A dental restoration, in particular tooth, crown or partial crown, is characterized by comprising a first layer of a first material which extends on the incisial side and a root side-extending second layer consisting of a second ceramic material, in that the first layer has a higher translucency and/or a lower strength than the second layer and that the first layer has a thermal expansion coefficient of about 0.2 μm/m*K to 0.8 μm/m*K lower than that of the second layer.

Further details, advantages and features of the invention result not only from the claims and the features disclosed therein alone and/or in combination but also from the following description of the example embodiments shown in the drawings.

DETAILED DESCRIPTION OF THE INVENTION

Figure 1A:
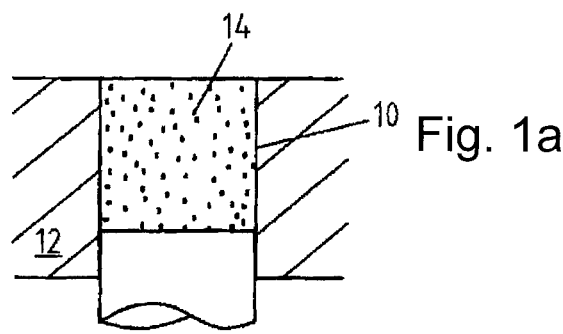
FIG. 1a shows a schematic of a device and a process step of the present invention performed using the device.

The teaching of the invention is illustrated by reference to the figures, in which the same elements are basically given the same reference numerals, wherein in particular dental restorations are produced from a ceramic material having a monolithic structure such that after complete sintering an immediately usable monolithic tooth replacement is available.

To this end, the invention provides for the preparation of a blank, which has regions of ceramic material with differing compositions and thus properties, has desired optical and mechanical properties according to the restoration to be produced, which, as mentioned, offer the possibility of immediate usage of the tooth replacement monolithically fabricated after full sintering without, for example, having to apply incisor material by hand.

Further, specifically desired strength values are attainable in the ranges in which high loads occur. Desired optical properties can be achieved.

Figure 1B:
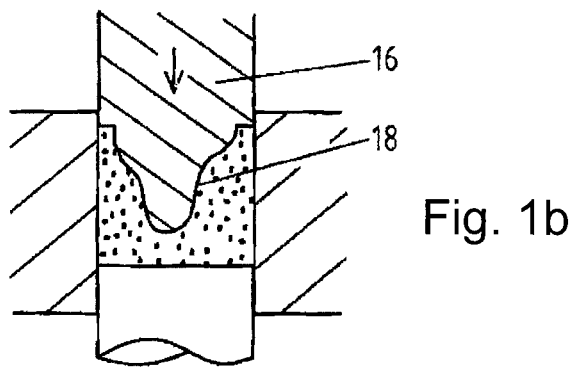
FIG. 1b shows a schematic of another process step of the present invention performed using the device shown in FIG. 1a, FIG. 1c shows a schematic of another process step of the present invention performed using the device shown in FIGS. 1a and 1b.
Figure 1C:
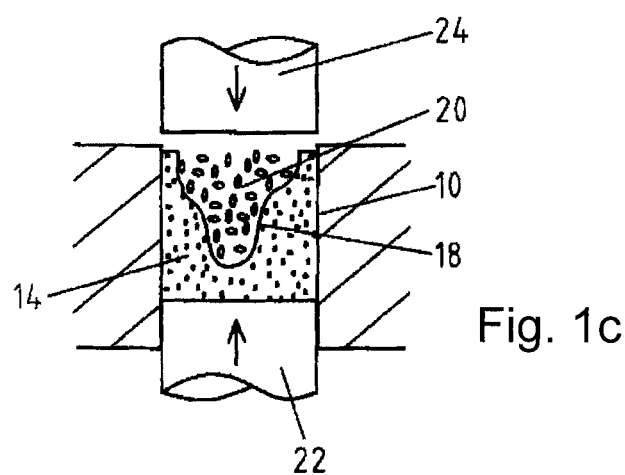
Figure 2:
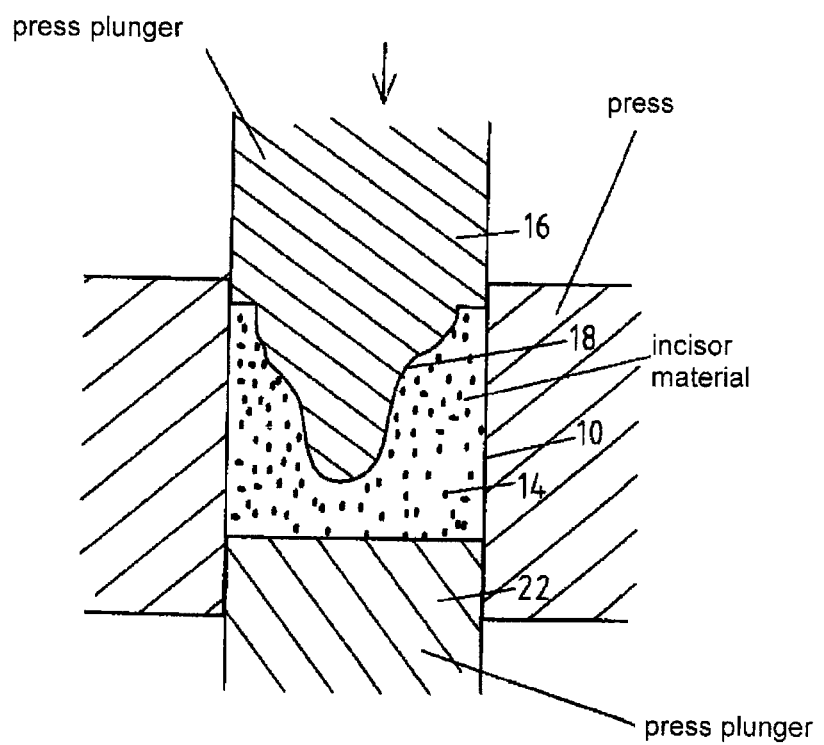
FIG. 2 shows FIG. 1b in greater detail.
Figure 3:
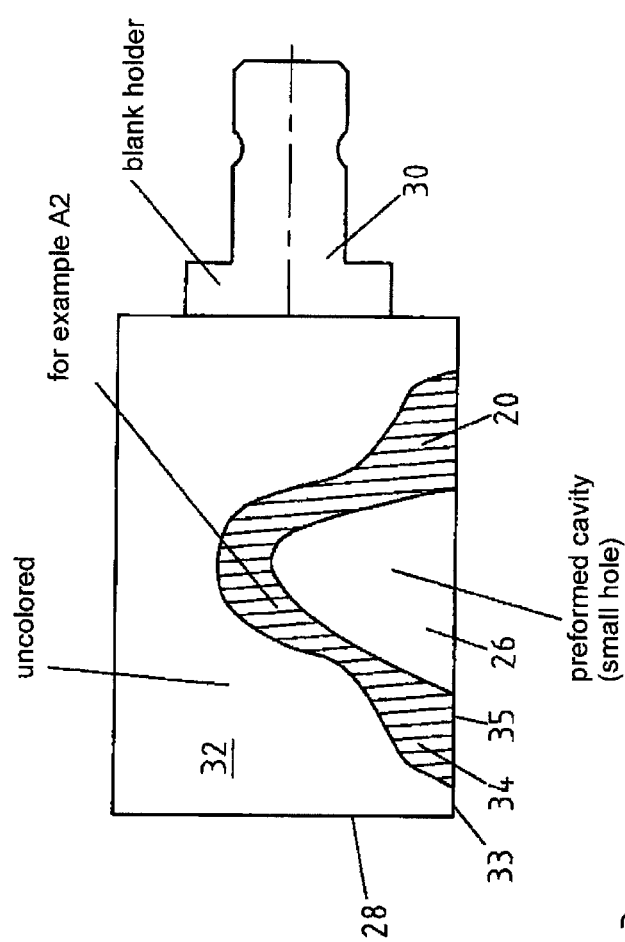
FIG. 3 shows a blank according to the present invention with regions of different material properties.

With reference to FIGS. 1 to 3, the manufacture of a blank will be described from which a dental restoration can be produced, in the example embodiment, a tooth.

Thus a pourable granulate in the form of a first ceramic material 14 is filled into the die 10 of a pressing tool 12, which is in particular a zirconium dioxide stabilized with yttrium oxide, which can have the following composition in wt %:

| | |
|---|---|
| $HfO_2$ | <3.0 |
| $Al_2O_3$ | <0.3 |
| $Y_2O_3$ | 7.0 to 9.5 |
| Color-imparting oxides: | 0-0.5 |
| Technically caused, unavoidable components ≤0.2 (such as $SiO_2$, $Fe_2O_3$, $Na_2O$) | |
| $ZrO_2$ | 100 − ($Y_2O_3$ + $Al_2O_3$ + $HfO_2$ + color-imparting oxides + technically caused, unavoidable components) |

A binding agent may also be added, but is not taken into consideration in the above percentage by weight values.

However, in particular it is provided for the composition to contain coloring oxides only in small amounts or not at all, for example ≤0.5 wt %, as the first ceramic material 14 is used as an incisor material, so that a high translucency is desired. As a result of the relatively high percentage of yttrium oxide, the tetragonal crystal phase is only 50 to 60% in the incisal region of the produced mold part, i.e., the dental restoration, and the remainder is the cubic and monoclinic crystal phase.

Then, by means of a press plunger 16 an open cavity 18 is formed in a material 14 or in a layer formed from this material. By means of the press plunger, the material 14 is displaced or slightly compacted. After the cavity 18 is formed (FIG. 1b), the press plunger 16 is removed and a second ceramic material 20 filled into the cavity 18, which may have one of the following compositions in wt %:

| | |
|---|---|
| $HfO_2$ | <3.0 |
| $Al_2O_3$ | <0.3 |
| $Y_2O_3$ | 4.5 to 7.0 |
| Color-imparting oxides: | 0-1.5 |
| Technically caused, unavoidable components ≤0.2 (such as $SiO_2$, $Fe_2O_3$, $Na_2O$) | |
| $ZrO_2$ | 100 − ($Y_2O_3$ + $Al_2O_3$ + $HfO_2$ + color-imparting oxides + technically caused, unavoidable components) |

Thereby, the coloring oxide or oxides should be present in an amount that results in a desired tooth color, since the dentine of the tooth to be produced is formed from the second ceramic material 20. The relatively low percentage of $Y_2O_3$ further ensures that the dentine of the fully-sintered tooth replacement has a high tetragonal phase content of at least 85%, preferably at least 90%, thus yielding a high strength.

After filling of the second ceramic material 20 into the cavity 18 (FIG. 1c), the materials 14, 20 respectively the layers or regions formed from these, are pressed in the die 10 by means of a lower or upper punch 22, 24 through which a compaction results. After pressing, the blank 28 has a density of approximately 3 $g/cm^3$. Pressing is preferably carried out at a pressure between 1000 bar and 2000 bar.

With regard to the ceramic materials 14, 20 it should also be noted that they have a bulk density between 1 $g/cm^3$ and 1.4 $g/cm^3$. After pressing, the density is approximately 3 $g/cm^3$.

FIG. 2 shows the contents of FIG. 1b) in more detail. It can be seen that the cavity 18 is formed through the press plunger 16 in the first ceramic material 14 respectively in the layer comprising the material. On the base side the die 10 is limited by the press plunger 22.

As can be seen from FIG. 3, a second cavity 26 can be formed in the second material 20 after its compression by the press plunger 22, 24 or optionally after the pre-sintering, for example by milling.

However, in accordance with FIG. 1c), it is also possible to form a corresponding second cavity 26 in the material 20, which completely fills the bottom-side open cavity 18, by means of a press plunger that is not shown.

Irrespective of whether the second cavity 26 is present or not, a pre-sintering of the blank 28 is carried out after pressing at a temperature in particular in the range between 800° C. and 1000° C. over a time period between 100 minutes and 150 minutes. There is initially a debinding and then pre-sintering. The density of the blank 28 after the pre-sintering is approximately 3 $g/cm^3$. The breaking strength of the pre-sintered blank 28 should be between 10 MPa and 60 MPa.

The blank 28 is provided with a holder 30, so that the blank 28 can be worked for example in a milling or grinding machine to derive a dental restoration such as a tooth from the blank 28, as explained with reference to FIG. 5. Thereby, the tooth to be produced is at least virtually laid in the blank 28 such that the incisal region runs into the region 32 formed by the first ceramic material 14 and the dentine region in sections runs into the second region 34 formed by the second ceramic material 20. The blank 28 is then worked taking this data into consideration.

Figure 4:
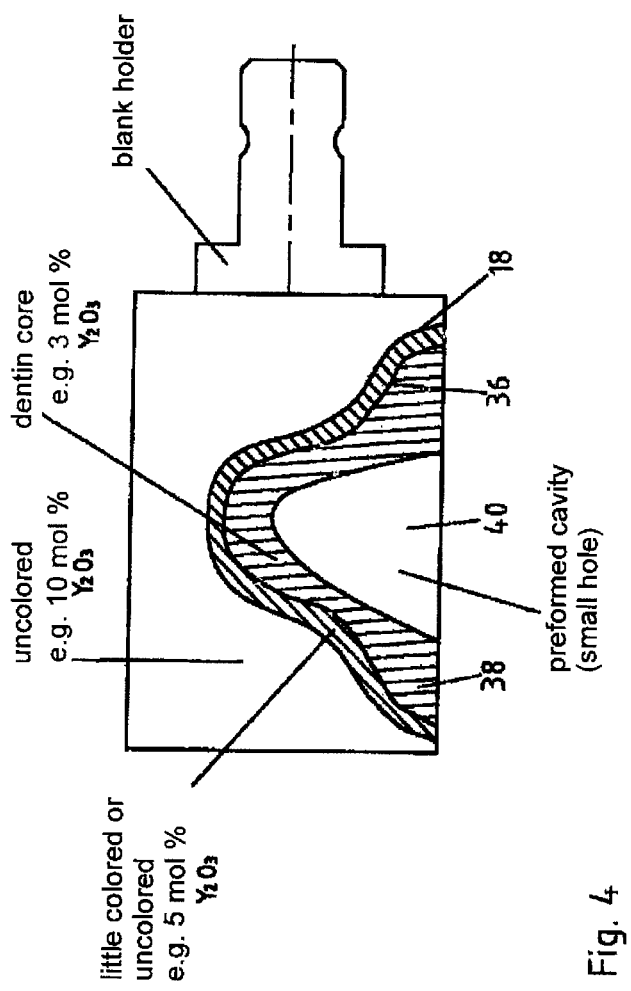
FIG. 4 shows another blank according to the present invention with regions of different material properties.

FIG. 4 illustrates that after filling of the first cavity 18 in the first ceramic material 14 and filling of the second ceramic material 20 into the cavity 18, a second cavity 36 is filled optionally in accordance with the procedure of FIG. 1b), so that a third ceramic material is filled into the cavity 36 so formed, which differs from the second ceramic material in its composition such that in particular a higher strength can be achieved. A cavity 40 may similarly be formed in the third ceramic material 38—as explained with reference to FIG. 3.

Figure 5:
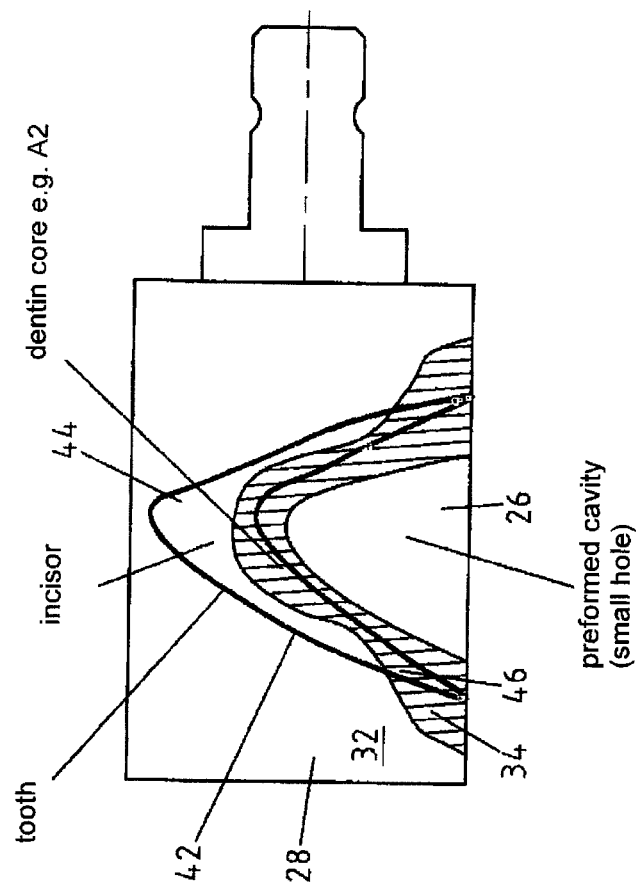
FIG. 5 shows a schematic of a blank according to the present invention with a tooth to be derived therefrom.

As FIG. 5 illustrates, a dental restoration, in the example embodiment, a tooth 42, is derived from the blank 28. For this purpose, with knowledge of the course of the first region 32 from the first ceramic material 14 and the second region 34 from the second ceramic material 20 in the blank 28 of the tooth 42 to be produced is virtually laid in the regions 32, 34 such that the incisor extends in the first region 32 and the dentine 46 extends into the second region 34.

After removal of the so virtually positioned tooth 42 from the blank 28, a tooth replacement is available, which in principle can be used directly, in particular does not require any veneer. A monolithic tooth 42 is prepared on the basis of the teaching of the invention. In this case, the preparation from the blank 28 is made easier in that the second region 34 already has an open cavity 26, as described with reference to FIG. 3 and as apparent from FIG. 5.

Figure 6:
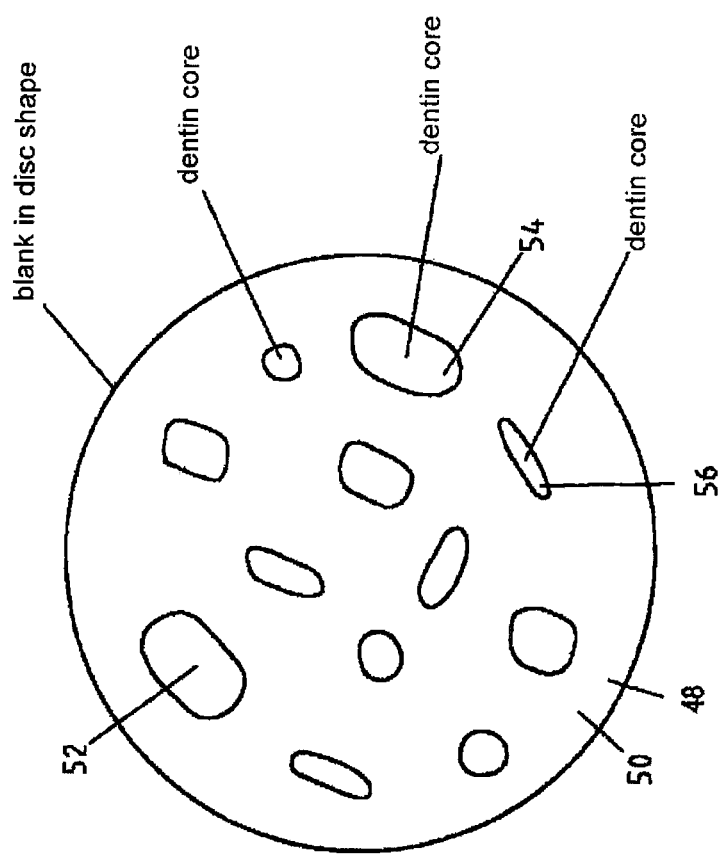
FIG. 6 shows a blank according to the present invention in a top view with a plurality of regions of different material properties.

The teaching of the invention introduces the possibility of forming a blank 48 that has a plurality of regions 52, 54, 56, that are made of the second and optionally the third ceramic material, and can have different geometries (FIG. 6), so that corresponding teeth of different geometries can be formed. The so-called second regions 50, 52, 54 formed from the second ceramic material 20 are embedded in the first ceramic material 48, i.e., are surrounded by this, as can be seen in particular also from the Figures. The second regions 50, 52, 54 are uncovered on the base side.

As can be seen in particular from FIGS. 2-4, the second regions have external geometries that taper starting from the bottom, i.e., from the base region. It may be referred to as a conus-like geometry, wherein the outer contour represents a freeform surface.

The base region 35/the base surface that limits it on the underside merges with the lower side of the base surface 33 of the first region 32.

To prepare the blank sections 52, 54, 56 also referred to as nests, it is necessary as described with reference to FIG. 1 to have corresponding open cavities in the layer made of the first material 14 and designated as the first region 50, so that the pourable second ceramic material 20 can be filled into the cavities in the manner described above and then the materials 14, 20 can be pressed together, i.e., compacted.

With regard to the physical properties of the materials 14, 20 it is to be noted that in addition to a difference in translucency and strength they should also have different thermal expansion coefficients. In particular, the invention provides for the first ceramic material 14 after full sintering to have a thermal expansion coefficient that is 0.2 μm/m*K to 0.8 μm/m*K lower than the second region 38, 52, 54, 56 formed from the second ceramic material 20. As a result of this a compression stress is generated in the first region 50, i.e., in the incisor material, which leads to an increase in strength.

With regard to the blanks 28, 48 it is to be noted that these can have a cuboid shape, for example the dimensions 18×15×25 mm or a disk shape, for example with a diameter of 100 mm, without thereby affecting the teaching of the invention. This brings in particular as explained by reference to FIG. 6 the advantage that, for example, a plurality of second regions 52, 54, 56 so-called dentine cores can be formed in a disk-shaped blank, to yield restorations of different geometries, but with a favorable layer course with respect to translucency and strength.

Since the position of one or more second regions 52, 56, i.e., nests, optionally with different geometries is known, they can be stored in a data record. Then, the restorations to be produced, which are available as CAD data sets, are positioned relative to and in the blank sections so that the tooth replacement can be derived from the blank by milling and/or grinding.

The invention claimed is:

1. A method for the preparation of a blank of a ceramic material comprising the steps of:
    filling into a mold a first ceramic material, wherein a layer of the first ceramic material is filled in a pourable condition into the mold, that in the layer, a first open cavity is formed;
    filling into the mold a second ceramic material of different composition, wherein the second ceramic material is filled in a pourable condition into the first open cavity;
    pressing the first and second materials together; and
    sintering the pressed materials to form a resultant blank;
    wherein the ceramic materials include zirconium dioxide doped with yttrium oxide ($Y_2O_3$), calcium oxide (CaO), magnesium oxide (MgO) and/or ceroxide ($CeO_2$), and
    wherein the first ceramic material differs from the material of the second ceramic material in terms of color and proportions of stabilized crystal forms present at room temperature.

2. The method according to claim 1, wherein after the step of filling the second ceramic material, a second open cavity is made therein.

3. The method according to claim 2, further comprising the step of filling into the second open cavity a third ceramic material, wherein the third ceramic material has a composition that differs from that of the first and/or second ceramic material.

4. The method according to claim 3, wherein the first ceramic material includes a percentage of yttrium oxide in the range 7.0 wt % to 9.5 wt % and the second ceramic material and/or the third ceramic material include a percentage of yttrium oxide in the range of 4.5 wt % to 7.0 wt %, and wherein the percentage of yttrium oxide in the first ceramic material is higher than that in the second or third material.

5. The method according to claim 3, wherein the first ceramic material, the second ceramic material, and/or the third ceramic material has a quotient of tetragonal crystal phase to cubic crystal phase of the zirconium dioxide in the materials after pre-sintering that is ≥1.

6. The method according to claim 1, wherein a plurality of first open cavities are formed in the layer of the first ceramic material and that the second ceramic material is filled into the plurality of first open cavities.

7. The method according to claim 6, wherein at least some of the plurality of open first cavities have different internal geometries.

8. The method according to claim 1, wherein the second ceramic material, after full sintering, has a thermal expansion coefficient that is 0.2 to 0.8 μm/m*K higher than that of the first ceramic material.

9. The method according to claim 1, wherein the internal geometry of the first open cavity is geometrically aligned with the course of a dental jaw region selected from the group consisting of a tooth stump or an abutment emanating from a jaw region that is to be provided with a restoration.

10. The method according to claim 1, further comprising the step of forming a dental restoration from the resultant blank, wherein the dental restoration includes a dentine region at least in part being formed from the second ceramic material and an incisal region being formed from the first ceramic material.

11. The method according to claim 1, wherein at least the second ceramic material is colored with at least one color-imparting oxide of elements selected from the group consisting of Pr, Er, Tb, Fe, Co, Ni, Ti, V, Cr, Cu, and Mn.

\* \* \* \* \*